(12) United States Patent
Seiberlich et al.

(10) Patent No.: US 12,196,828 B2
(45) Date of Patent: Jan. 14, 2025

(54) MAGNETIC RESONANCE FINGERPRINTING USING ROSETTE TRAJECTORIES FOR FAT FRACTION MAPPING

(71) Applicant: REGENTS OF THE UNIVERSITY OF MICHIGAN, Ann Arbor, MI (US)

(72) Inventors: Nicole Seiberlich, Ann Arbor, MI (US); Yun Jiang, Ann Arbor, MI (US); Jesse Hamilton, Ann Arbor, MI (US); Yuchi Liu, Ann Arbor, MI (US)

(73) Assignee: REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 67 days.

(21) Appl. No.: 17/990,621

(22) Filed: Nov. 18, 2022

(65) Prior Publication Data
US 2024/0168115 A1   May 23, 2024

(51) Int. Cl.
*G01V 3/00* (2006.01)
*A61B 5/00* (2006.01)
*A61B 5/055* (2006.01)
*G01R 33/48* (2006.01)
*G01R 33/50* (2006.01)

(52) U.S. Cl.
CPC ............ *G01R 33/50* (2013.01); *A61B 5/0044* (2013.01); *A61B 5/055* (2013.01); *G01R 33/4824* (2013.01); *G01R 33/4828* (2013.01); *A61B 2576/023* (2013.01)

(58) Field of Classification Search
CPC ............ G01R 33/3415; G01R 33/543; G01R 33/5659; G01R 33/36; A61B 5/055

USPC .......................................................... 324/309
See application file for complete search history.

(56) References Cited

U.S. PATENT DOCUMENTS

| | | | |
|---|---|---|---|
| 2015/0301138 A1* | 10/2015 | Griswold | G01R 33/56366 324/309 |
| 2015/0302579 A1* | 10/2015 | Griswold | H04N 19/85 382/128 |
| 2017/0181656 A1* | 6/2017 | Reeder | A61B 5/055 |
| 2019/0353718 A1* | 11/2019 | Griswold | G01R 33/561 |
| 2019/0353731 A1* | 11/2019 | Liu | G01R 33/54 |

OTHER PUBLICATIONS

Farrelly et al., ECG-gated multiecho Dixon fat-water separation in cardiac MRI: Advantages over conventional fat-saturated imaging., Am. J. Roentgenol., 199:W74-83 (2012).

(Continued)

*Primary Examiner* — Walter L Lindsay, Jr.
*Assistant Examiner* — Frederick Wenderoth
(74) *Attorney, Agent, or Firm* — MARSHALL, GERSTEIN & BORUN LLP

(57) ABSTRACT

Methods and systems perform magnetic resonance fingerprinting (MRF) that provides tissue characterization through simultaneous quantification of water tissue properties and proton density fat fraction (PDFF), by using water-only and fat-only images from MRF. MRF is performed using rosette trajectories scanning k-space to effectively isolate water tissue and fat tissue, by separating these rosette trajectories into individual segments that are then analyzed to enable signals from fat tissue to be distinguished from water.

12 Claims, 8 Drawing Sheets
(2 of 8 Drawing Sheet(s) Filed in Color)

(56) References Cited

OTHER PUBLICATIONS

Hamilton et al., Investigating and reducing the effects of confounding factors for robust T1 and T2 mapping with cardiac MR fingerprinting, Magn. Reson. Imaging, 53:40-51 (2018).

Hamilton et al., MR fingerprinting for rapid quantification of myocardial T1, T2, and proton spin density, Magn. Reson. Med., 77:1446-1458 (2017).

Hines et al., T1 independent, T2* corrected MRI with accurate spectral modeling for quantification of fat: validation in a fat-water-SPIO phantom, J. Magn. Reson. Imaging, 30:1215-1222 (2009).

Jaubert et al., Water-fat Dixon cardiac magnetic resonance fingerprinting, Magn. Reson. Med., 83(6):2107-2123 (2019).

Keenan et al., Multi-site, multi-platform comparison of MRI T1 measurement using the system phantom, Proc. Int. Soc. Magn. Reson. Med., 24:3290 (2016).

Kellman et al., Multiecho dixon fat and water separation method for detecting fibrofatty infiltration in the myocardium. Magn. Reson. Med., 61:215-221 (2008).

Liu et al., Fat quantification with Ideal gradient echo imaging: Correction of bias from T1 and noise. Magn. Reson. Med., 58:354-364 (2007).

Liu et al., Myocardial T1 and T2 quantification and water-fat separation using cardiac MR fingerprinting with rosette trajectories at 3T and 1.5T, Magn. Reson. Med., 85(1):103-119 (2021).

Rakow-Penner et al., Relaxation times of breast tissue at 1.5T and 3T measured using Ideal, J. Magn. Reson. Imaging, 23:87-91 (2006).

Russek et al., Characterization of NIST/ISMRM MRI system phantom., Proc. Int. Soc. Magn. Reson. Med., 20:2456 (2012).

Tsao et al., Hierarchical Ideal: fast, robust, and multiresolution separation of multiple chemical species from multiple echo times, Magn. Reson. Med., 70:155-159 (2013).

\* cited by examiner

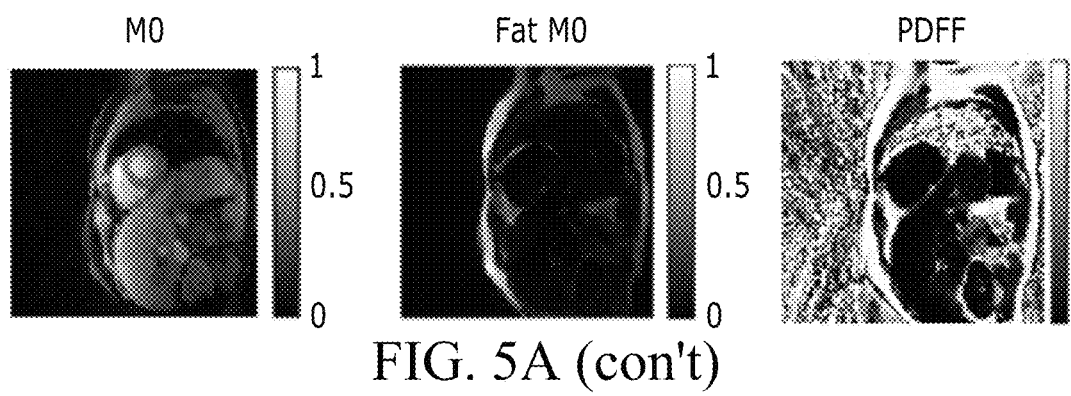
FIG. 5A (con't)
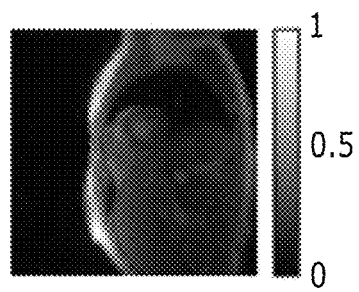
FIG. 5B (con't)

MAGNETIC RESONANCE FINGERPRINTING USING ROSETTE TRAJECTORIES FOR FAT FRACTION MAPPING

STATEMENT OF GOVERNMENT SUPPORT

This invention was made with government support under HL094557 awarded by the National Institutes of Health and 2002887 awarded by the National Science Foundation. The government has certain rights in the invention.

FIELD OF THE DISCLOSURE

The invention generally relates to magnetic resonance fingerprinting techniques and, more particularly, to generating quantitative tissue property maps that include isolated fat issue maps from a single pulse sequence scan using magnetic resonance fingerprinting techniques.

BACKGROUND

The background description provided herein is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

In non-Cartesian magnetic resonance imaging (MRI), fat signals are a dominant source of off-resonance artifacts. Fat can cause blurring in images collected along non-Cartesian sampling schemes, such as spiral and radial scans, instead of simply a spatial shift in the readout direction as in Cartesian MRI. In order to reduce these chemical shift artifacts due to fat, fat suppression techniques can be used to destroy fat signals before acquisition by exploiting the differences in $T_1$ or chemical shift of water and fat, resulting in dark areas of fat in the image. Water excitation techniques can also be used to select water but not fat protons by means of spectral spatial pulses. Alternatively, water—fat separation techniques provide fat images in addition to water images by acquiring both water and fat signals and then attempting to separate them with dedicated post-processing algorithms. These techniques typically use multi-echo Dixon methods or special data collection trajectories such as rosette. Water—fat separation provides valuable information in various clinical applications. Especially in the heart, removal of the fat signals can improve visualization of the anatomical structure of the heart and is also important for imaging coronary arteries. Fat identification in the myocardium has potential value in diagnosing intra-myocardial fat and fibro-fatty infiltration and lipomas.

Thus far, however, techniques measuring fat in MRI, measure a combined water-fat separation in an image and take multiple images or multiple scans. There is a need for an efficient approach for generating tissue maps, such as water $T_1$ and $T_2$ maps, along with proton density fat fraction maps, using a single scan for comprehensive tissue characterization.

SUMMARY OF THE INVENTION

The present techniques provide systems and methods for performing magnetic resonance fingerprinting (MRF). The present techniques enable cardiac MRF (cMRF) using a rosette-based readout for water $T_1$ and $T_2$ mapping and for fat fraction mapping. The systems and methods enable simultaneous myocardial $T_1$ and $T_2$ quantification and fat fraction mapping using a single MRF scan. While many MRF approaches do not distinguish water from fat, the present techniques are able to expressly isolate fat signals from water signals, and elimination of the signal from fat can be used to reduce mapping errors caused by water-fat partial volume effects. Moreover, the present techniques are able to yield quantitative proton density fat fraction (PDFF) mapping, which may provide additional value in diagnosing disease. Previous techniques incorporated the Dixon method into an cMRF framework using multi-echo radial acquisitions to enable $T_1$, $T_2$, and PDFF quantification. Other previous work demonstrated that water-fat separation can be achieved along with myocardial $T_1$ and $T_2$ mapping using cMRF with rosette trajectories. However, the present techniques are able to implement rosette trajectories with cMRF extended to enable simultaneous myocardial $T_1$, $T_2$, and PDFF mapping from a single scan.

In an aspect, a method for performing magnetic resonance fingerprinting (MRF) includes: obtaining, using a magnetic resonance scanning device, MRF data of a region of interest in a sample and resulting from provision of a MRF pulse sequence to the sample, wherein obtaining the MRF data includes sampling a k-space using a rosette trajectory formed of a plurality of lobes; calculating a MRF dictionary of signal profiles based on the MRF pulse sequence applied; comparing the MRF dictionary to the MRF data to generate $T_1$ and $T_2$ maps from water corresponding to the region of interest; separating MRF data into a plurality of MRF data segments, each MRF data segment corresponding to a different segment of the plurality of lobes of the rosette trajectory; processing the plurality of MRF data segments to generate an isolated fat signal image, and generating, using the $T_1$ and $T_2$ maps from water and the isolated fat signal image, a proton density fat fraction map corresponding to the region of interest; and generating a report of the $T_1$ and $T_2$ maps and the proton density fat fraction map.

In an aspect, each of the plurality of lobes of the rosette trajectory samples a central region of the k-space.

In an aspect, each of the segments of the plurality of lobes of the rosette trajectory samples the central region of the k-space.

In an aspect, at least some of the segments of the plurality of lobes of the rosette trajectory samples the central region of the k-space.

In an aspect, the plurality of lobes of the rosette trajectory comprises at least 3 lobes. In an aspect, the plurality of lobes of the rosette trajectory comprises 8 lobes.

In an aspect, comparing the plurality of MRF data segments to the MRF dictionary to generate an isolated fat tissue mapping comprises: projecting each MRF data segment onto a low dimensional subspace derived from the MRF dictionary In an aspect, the MRF dictionary of signal profiles correspond to a cardiac rhythm.

In an aspect, generating the report of the $T_1$ and $T_2$ maps and the proton density fat fraction map comprises: displaying the $T_1$ and $T_2$ maps and the proton density fat fraction map on a digital display In another aspect, a non-transitory computer-readable storage medium storing executable instructions that, when executed by a processor, cause a computer to: obtain, using a magnetic resonance scanning device, MRF data of a region of interest in a sample and resulting from provision of a MRF pulse sequence to the sample, wherein obtaining the MRF data includes sampling a k-space using a rosette trajectory formed of a plurality of lobes; calculate a MRF dictionary of signal profiles based on the MRF pulse sequence applied; compare the MRF dictionary to the MRF data to generate $T_1$ and $T_2$ maps from water corresponding to the region of interest; separate MRF data into a plurality of MRF data segments, each MRF data segment corresponding to a different segment of the plurality of lobes of the rosette trajectory; process the plurality of MRF data segments to generate an isolated fat signal image, and generate, using the $T_1$ and $T_2$ maps from water and the isolated fat signal image, a proton density fat fraction map corresponding to the region of interest; and generate a report of the $T_1$ and $T_2$ maps and the proton density fat fraction map.

In an aspect, each of the plurality of lobes of the rosette trajectory samples a central region of the k-space.

In an aspect, each of the segments of the plurality of lobes of the rosette trajectory samples the central region of the k-space.

In an aspect, at least some of the segments of the plurality of lobes of the rosette trajectory samples the central region of the k-space.

In an aspect, wherein the plurality of lobes of the rosette trajectory comprises at least 3 lobes.

In an aspect, the plurality of lobes of the rosette trajectory comprises 8 lobes.

In an aspect, the non-transitory computer-readable storage medium of claim 10, storing executable instructions that, when executed by the processor, cause the computer to project each MRF data segment onto a low dimensional subspace derived from the MRF dictionary.

In an aspect, the MRF dictionary of signal profiles correspond to a cardiac rhythm.

In an aspect, the non-transitory computer-readable storage medium of claim 10, storing executable instructions that, when executed by the processor, cause the computer to display the $T_1$ and $T_2$ maps and the proton density fat fraction map on a digital display.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The figures described below depict various aspects of the system and methods disclosed herein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

FIG. 5A illustrates $T_1$ tissue mappings, $T_2$ tissue mappings, $M_0$ isolated water mappings, Fat M0 isolated fat tissue mappings, and PDFF measurements in the fat fraction phantom, in accordance with an example of the present techniques herein. FIG. 5B illustrates $T_1$ tissue mappings, $T_2$ tissue mappings, and M0 isolated water mappings, in accordance with a conventional spiral cardiac MRF technique. FIG. 5C illustrates $T_1$ tissue mappings and $T_2$ tissue mappings, in accordance with a conventional clinical $T_1$ and $T_2$ mapping techniques.

DETAILED DESCRIPTION

Figure 1:
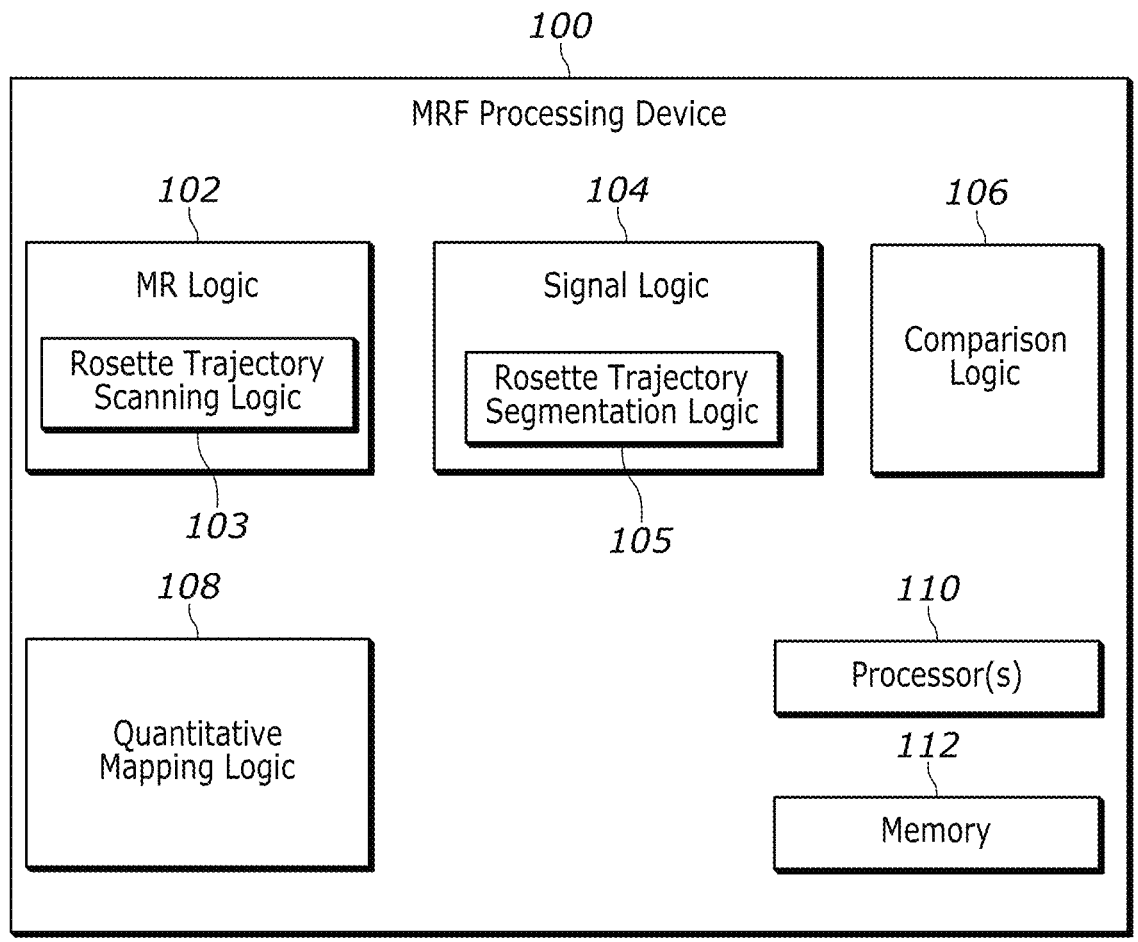
FIG. 1 illustrates an example magnetic resonance fingerprinting (MRF) processing device for performing tissue imaging analysis in particular isolating fat tissue property maps, in accordance with an example herein.

The present techniques provide systems and methods for magnetic resonance fingerprinting (MRF), where tissue often has both water and fat content that makes tissue mapping a challenge. The present techniques enable efficient tissue characterization through simultaneous quantification of tissue properties including water $T_1$ and $T_2$ and proton density fat fraction (PDFF), i.e., using water-only and fat-only images from MRF in which fat content in tissue has been isolated from water content. In particular, the present techniques combine MRF techniques with rosette trajectories scanning k-space to effectively isolate water vs. fat tissue and greatly improve visualization of anatomical structures. For example, rosette trajectories are separated into individual segments that are then mapped to captured scan data to enable signals from fat tissue to be distinguished from those of water. These techniques allow for a comprehensive tissue characterization using a single scan of a region of interest.

In an embodiment, the present techniques include systems and methods for performing magnetic resonance fingerprinting (MRF) that include obtaining, using a magnetic resonance scanning device, MRF data of a region of interest in a sample where that MRF data results from applying an MRF pulse sequence to the sample. Further, obtaining the MRF data includes sampling a k-space using a rosette trajectory formed of a plurality of lobes. The techniques further include obtaining a MRF fingerprint dictionary of signal profiles and comparing the MRF fingerprint dictionary to the MRF data. From that comparison, high resolution tissue water-specific property maps are generated for the region of interest, for example, $T_1$ and $T_2$ maps. Additionally, the MRF data is separated in a plurality of MRF data segments, each MRF data segment corresponding to a different segment of the plurality of lobes of the rosette trajectory. Each MRF data segment may be input to an IDEAL toolbox, e.g., a known algorithm for water-fat separation to generate a PDFF map. Separately, the MRF data (non-segmented data) can be compared to an MRF fingerprint dictionary to generate $T_1$ and $T_2$ tissue maps and this may be achieved in parallel to the MRF data segment pipeline. After the water-only $T_1$ and $T_2$ maps and the PDFF maps have been generated, they can be displayed individually to a professional to assess the region of interest.

As previously mentioned, conventional MRF techniques have been unable to sufficiently isolate fat content from water content in tissue property maps. Conventional MRF techniques measure water and fat signals together. Conventional MRI techniques can be used to separate water and fat, but only through using the Dixon method, spectral pulses, or special trajectories. No one has been able to use MRF techniques to isolate water from fat content for tissue mapping.

It is an objective of the present disclosure to overcome these limitations by providing MRF analysis that relies upon special trajectories, such as rosette trajectories, separated into trajectory segments that are analyzed separately and alongside MRF data over an entire scan region which is compared against fingerprinting dictionaries. Trajectory segments may scan a central region of k-space and in some examples scanning in and out of that central region of k-space to isolate fat from water in a scanned region of interest.

FIG. 1 illustrates an MRF processing device 100, for example, as may be used to control using a magnetic resonance scanning device to analyze MR images, in accordance with various techniques herein. The MRF processing device 100 includes one or more logic modules 102, 104, 106, 108, and/or 110, and that represents an implementation of the MRF acquisition system 102. Depending on the implementation, the logic modules 102, 104, 106, 108, and/or 110 may be implemented in the MRF processing device 100 as hardware, software, firmware, or some combination of such. MRF processing device 100 simultaneously quantifies MR parameters including water $T_1$, water $T_2$, isolated fat content, and isolated water content for a sample to which the MRF processing device 100 applies an MRF pulse sequence. The isolated fat content together with the isolated water content can be used to calculate the proton density fat fraction map. In various embodiments, the MRF processing device 100 provides an MR image that facilitates identifying tissues, including isolating fat and water tissue, based on their relative hypo-intense or hyper-intense appearance on an MR image (e.g., $T_1$ weighted image, $T_2$ weighted image, proton density fat fraction, etc.).

MRF processing device 100 includes a MR logic module 102. The MR logic module 102 controls operation of the magnetic resonance scanning device to repetitively and variably sample an object (e.g., a tissue region of a subject) in a (k, t, E) space to acquire a set of MR signals that may have non-constant amplitude and/or phase. For the (k, t, E) space, the k may be a point in k-space representing a spatial frequency of an MR image. In some implementations, the MR logic 102 may determine the value of k based on a Fourier Transform (FT) of the MR image. The t in the (k, t, E) space represents time, and the E represents one or more MR parameters for the MR image in question. Members of the set of MR signals are associated with different points in the (k, t, E) space. In different examples, the different points are sampled according to a plan where t and/or E varies non-linearly and/or in a non-constant manner.

The MR logic module 102 controls sampling of the object using an MR pulse sequence containing at least one variable sequence block. Each sequence block contains an excitation phase, a readout phase, and a waiting phase, and the duration of the sequence block is referred to as the repetition time (TR). The excitation phase applies radiofrequency (RF) energy and a gradient waveform magnetic field to a volume of one or more resonant species. The readout phase samples the signal resulting from the excitation phase simultaneously for all resonant species. The waiting phase is a pause before the beginning of the next sequence blocks.

In some examples, the MR logic module 102 designs and generates MR pulse sequences more attuned with either of the $T_1$ tissue map or the $T_2$ tissue map. For example, the signal may be more $T_1$-weighted or more $T_2$-weighted. In still further examples, the MR logic module 102 may generate pulse sequences more attuned to fat isolation and/or water isolation. In some examples, the MR logic module 102 may acquire the signal with sequence blocks of varying RF excitation energy, varying repetition times, varying waiting times, varying diffusion gradient moments, and varying readout parameters. Readout parameters include the sampling pattern, sampling density, and extent of k-space covered. Examples of pulse sequences include steady state free precession and balanced steady state free precession.

Figure 3:
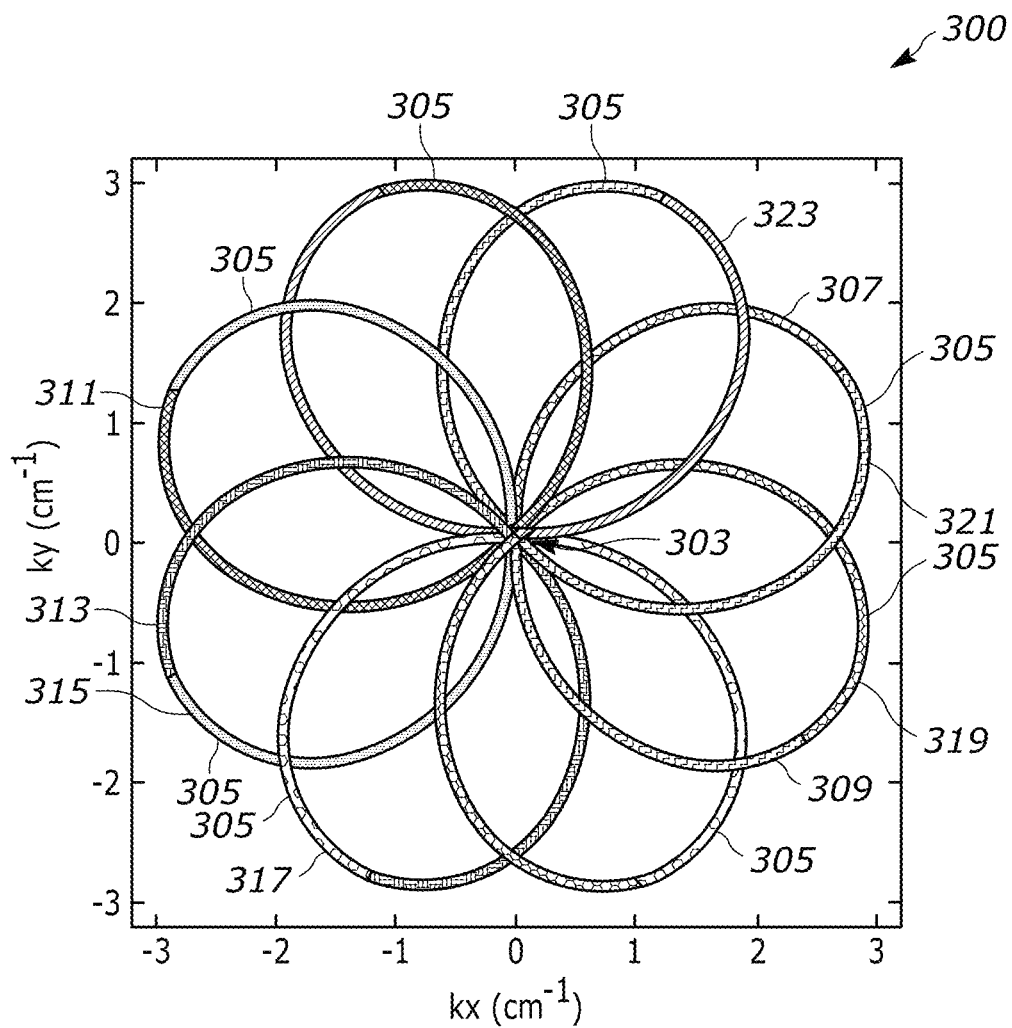
FIG. 3 is a plot of an example rosette trajectory, showing lobes, and examples of each segment used to generate multi-echo images indicated by different colors, in accordance with an example herein.

In the illustrated example, the MR logic module 102 includes a scanning logic, in particular a rosette trajectory scanning logic 103 that applies a rosette sampling pattern trajectory in scanning a k-space. As the rosette trajectory scans the k-space, off-resonance spins accumulate phase, which is determined by the off-resonance frequency and readout timing; on-resonance spins are not associated with a phase term. The scanning logic 103 forms the rosette trajectory of a plurality of lobes that each return to the center of k-space. That is, the rosette trajectory returns to the center of the k-space multiple times during a readout; each time the trajectory crosses the center of k-space, signals at some off-resonance frequencies can destructively interfere due to their phase differences if the timing is set properly. To perform readout using a rosette trajectory, the MR logic module 102 may set MR pulse sequence parameters, such as a constant TR and TE and number of excitations per heartbeat for the rosette trajectory. In some examples, the scanning logic 103 may apply different rosette trajectory patterns, in which one or more of these MR pulse sequence parameters may be adjusted so different MR pulse sequences are used for each different rosette trajectory pattern. An example rosette trajectory 300 is illustrated in FIG. 3.

In the illustrated example, the MRF processing device 100 also includes a signal logic module 104. Signal logic module 104 produces an MR signal evolution from the acquired MR signals from the MR logic 102. The signal evolution may include a number of MR signals acquired over a period of time. The set of MR signals may include transient-state signals associated with the MRF pulse sequence, a free induction decay signal, and a spin echo signal. The comparison logic module 106 compares reference information (e.g., stored in the memory 112 or in the comparison logic 106) with the produced MR signal evolution or information associated with the produced MR signal evolution. In some implementations, the comparison logic module 106 determines whether a match exists between signals included in the reference information and at least one of the produced MR signal evolution or information associated with the produced MR signal evolution based on whether the comparison logic module 106 determines there to be an exact match. In various examples, the reference information include dictionaries of signal profiles, such as signal profiles corresponding to cardiac rhythms, allowing for cMRF analysis.

In other implementations, an exact match is not necessary, and the comparison logic module 106 may determine that there exists a match where measured signals are similar to the reference information. Depending on the implementation, a match may be the signal that most closely matches another signal and/or the first signal that matches another signal to within a threshold. A match may be found by template matching, pattern matching, iterative reconstructions, machine learning approaches or other comparison approaches. The reference information may be, for example, a previously acquired signal evolution, a simulated signal evolution, an item derived from a signal evolution other than the produced MR signal evolution, and/or any other similar information. The reference information may include signal evolutions from different tissue types (e.g., healthy, diseased, advanced disease, etc.). In some examples, that reference information pertains to myocardial (cardiac muscle) tissue.

In the illustrated example, the signal logic 104 includes a rosette trajectory segmentation logic 105 that separates the captured MRF scan data into a plurality of segments corresponding to the segment portions of the rosette pattern.

To generate MRF tissue maps, the quantitative mapping logic module 108 is configured to generate, from the magnetic resonance data captured at MR logic 102, high-resolution tissue property maps of the sample, in accordance with techniques herein. The quantitative mapping logic module 108 may produce one or more quantitative maps of tissue properties associated with the object being scanned, for example, quantitative maps for $T_1$, $T_2$, proton density, and diffusion, based at least in part on the stored signal evolution that matches the MR signal evolution. Further, the quantitative mapping logic module 108 produces isolated fat tissue maps, which along with water tissue maps are used to generate proton density fat fraction (PDFF) maps.

The MR parameters may be retrieved from a data store that links stored MR parameters to the reference information, which may be in the form of fingerprint dictionaries 107. Quantitative mapping logic module 108 may also display the quantitative maps or cause the quantitative maps to be displayed. In some examples, multiple tissue property maps are generated simultaneously by the module 108.

While comparison logic module 106 and quantitative logic module 108 are illustrated as being part of MRF processing device 100, in some examples, the comparison logic module 106 and quantitative mapping logic module 108 may reside in an apparatus separate from the MRF processing device 100. In such examples, MRF processing device 100 may provide MR signals to the separate apparatus housing comparison logic module 106 or quantitative mapping logic module 108. In further examples, comparison logic module 106 and/or quantitative mapping logic module 108 may reside in separate apparatuses.

While shown as separate logic modules 102-108, each of which may be implemented in hardware having one or more processors and memory, in some examples, the MRF processing device 100 is implemented having one or more processors 110 that may implement the operation of the logic modules 102-108. Further the processing device 100 may have a computer-readable memory 112 having instructions that may be executed by the one or more processors 112 and/or logic modules 102-108 to perform the methods and processes described herein.

Figure 2:
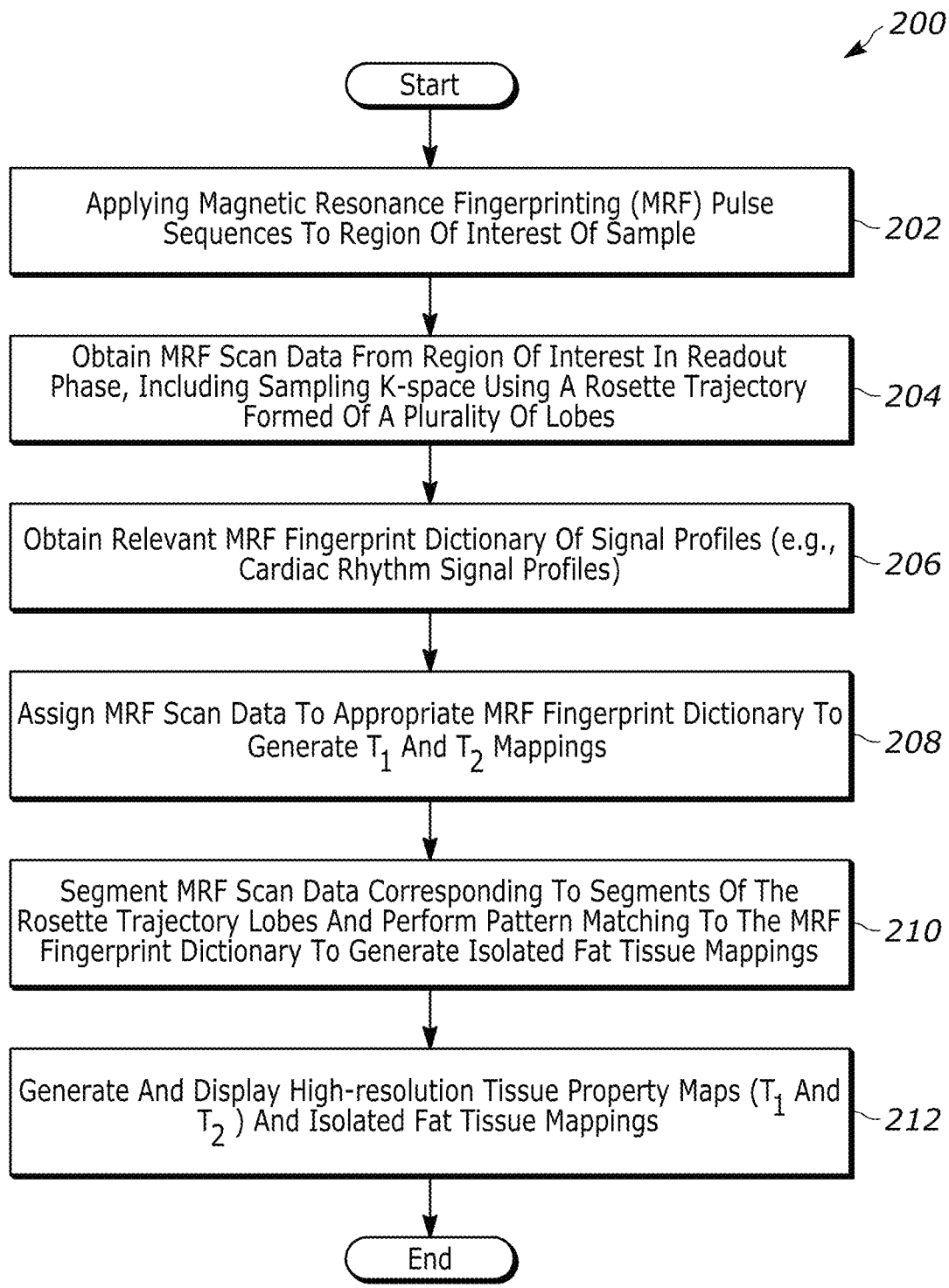
FIG. 2 illustrates an example process for performing magnetic resonance fingerprinting (MRF) that includes imaging analysis and tissue property map generation of isolated fat tissue property maps, in accordance with an example herein.

FIG. 2 illustrates an example method 200 for performing magnetic resonance fingerprinting and as may be performed by the MRF processing device 100, in an example. At a block 202, one or more fingerprinting pulse sequences are generated and scanned across a region of interest of a sample, where, for example, the MRF pulse sequences are defined by pulse parameters set by the MR logic 102. At a block 204, MRF scan data resulting from the MRF pulse sequences of block 202 are obtained. To obtain the MRF scan data, the block 204 includes a readout phase that applies a special pattern, in the illustrated example a rosette trajectory, to generate MRF scan data. FIG. 3 illustrates an example rosette trajectory 300 formed of 8 lobes 305. In the illustrated example, each lobe 305 scans through a central region 307 of k-space. Further each lobe 305 extends to an outer region of k-space, where each lobe 305 extends in a different radial direction from the central region 307. Collectively, the lobes 305 are spaced equally apart and are symmetric with another lobe around a centroid of het k-space. The pattern of the rosette trajectory and the numbers of lobes thereof may vary. In some examples, the rosette trajectory includes at least 5 lobes, at 6 least lobes, at least 7 lobes, or at least 8 lobes. The lobes may be spaced equally apart as shown here, but may also have a variable spacing. The lobes may cover the same extent of k-space as shown here, but may also cover different extents of k-space or have variable shapes. A rosette trajectory is any k-space data collection trajectory that alternates between sampling the center and high frequency (outer) portions of k-space at least once, where the acquisition is continuous throughout this time. While example rosette trajectories are shown by example, the present techniques included any other type of rosette trajectory.

At a block 206, a relevant MRF dictionary of signal profiles is calculated (or more than one dictionary is calculated), where in various examples herein, those signal profiles are from cardiac rhythms for myocardial tissue.

The process 200, at a block 208, assigns the scan data to an appropriate dictionary of signal profile patterns, for example, to match the MRF scan data to a signal profile in the MRF dictionary to generate $T_1$ and $T_2$ mappings. In one embodiment, the MRF scan data corresponding to the MRF pulse sequence is compared to the MRF dictionary of signal profiles until a match is found. In other implementations, an exact match is not necessary, and the block 208 may determine that there exists a match where signals are similar. Depending on the implementation, a match may be the signal that most closely matches another signal and/or the first signal that matches another signal to within a threshold. A match may be found by template matching, pattern matching, iterative reconstruction, machine learning approaches or other comparison approaches. In the illustrated example, the comparison is between MR signal evolutions and an MRF dictionary made up of reference signals with different $T_1$ and $T_2$ values and, as a result, water $T_1$ and $T_2$ maps are generated at the block 208.

Whereas the block 208 generates high resolution tissue map data for water $T_1$ and $T_2$, and fat tissue is isolated from water tissue, the process 200 performs a segmentation level analysis of the rosette trajectory. For example, at the block 210, the process 200 segments the obtained MRF scan data into segments corresponding to segments of the rosette trajectory. In particular, these segments may be non-overlapping segments of the various lobes forming the rosette trajectory. FIG. 3 illustrates various segments for the 8 lobes 305. In the illustrated example, the 8 lobes are segmented into 9 segments, each corresponding to a segment of the MRF scan data. Each of the segments sample a central region of the k-space. Some of the segments (specifically two segments 307 and 309) sample either outward from or inward to the central region of k-space. The other segments (specifically seven segments 311-323) sample inward to and outward from the central region of k-space. Thus, not all segments are equally shaped, although in the illustrated example, all sample a central region. In an example, the MRF data segments were input to the IDEAL process to generate a PDFF. The IDEAL process is a known algorithm for water-fat separation that is used to generate a PDFF map, and performs an iterative decomposition of water and fat with echo asymmetry and least-squares estimation for separating fat and water.

At a process 212, a report of the high resolution tissue maps water $T_1$ and $T_2$ are generated and displayed along with the PDFF map. Examples generated digital reports are described in reference to FIGS. 4A-4C and 5A-5C.

EXAMPLE

Example implementations of the processing device 100 and the method 200 are now described.

A rosette trajectory with eight lobes and a readout duration of 7.7 ms was designed to suppress fat signals at −220 Hz for 1.5 T. A previously reported 15-heartbeat ECG-triggered 2D cMRF sequence structure was used (see, Liu, Y., Hamilton, J., Eck, B., Griswold, M. & Seiberlich, N. Myocardial T1 and T2 quantification and water—fat separation using cardiac MR fingerprinting with rosette trajectories at 3 T and 1.5 T. Magn. Reson. Med. (2021)). Spatial resolution of 1.6×1.6 mm$^2$ and a slice thickness of 8 mm were employed in all experiments. After water-fat separation and B0 correction, water and fat $T_1$ and $T_2$ maps were generated by matching undersampled images (one image per TR) to an MRF fingerprint dictionary that modeled the patient's cardiac rhythm, as described in Liu, Y., Hamilton, J., Eck, B., Griswold, M. & Seiberlich, N. Myocardial T1 and T2 quantification and water—fat separation using cardiac MR fingerprinting with rosette trajectories at 3 T and 1.5 T. Magn. Reson. Med. (2021). To generate quantitative proton density fat fraction (PDFF) maps, the 8-lobe trajectory was divided into 9 segments (FIG. 1a). MRF scan data from each segment were projected onto a low-dimensional subspace derived from the singular value decomposition (SVD) of the MRF fingerprint dictionary. Subspace images corresponding to the first singular value were retained; images from each of the 9 rosette segments served as multi-echo images and were used to generate a PDFF map using Hierarchical IDEAL.

All experiments were performed on a 1.5 T scanner (from Siemens Sola, Erlangen, Germany). The proposed rosette cMRF process was applied on an in-house built fat fraction phantom and the fat fraction results were compared with 3-point Dixon GRE measurements with optimal echo times at 1.5 T (1.9/3.4/4.9 ms). $T_1$ and $T_2$ measurements in the $T_2$ layer of the ISM RM/NIST MRI system phantom were compared with gold standard values measured using inversion-recovery and single-echo spin-echo methods. Twelve healthy subjects were scanned after written informed consent in this IRB-approved study. Mid-ventricular level short axis slices in the heart were acquired using the proposed rosette cMRF sequence and the original spiral cMRF sequence. Conventional $T_1$ and $T_2$ mapping scans (MOLLI and $T_2$-prepared bSSFP) were also performed on eight of the subjects. Significant difference between different methods was considered with P<0.05 in a student's t-test.

Figure 4A:
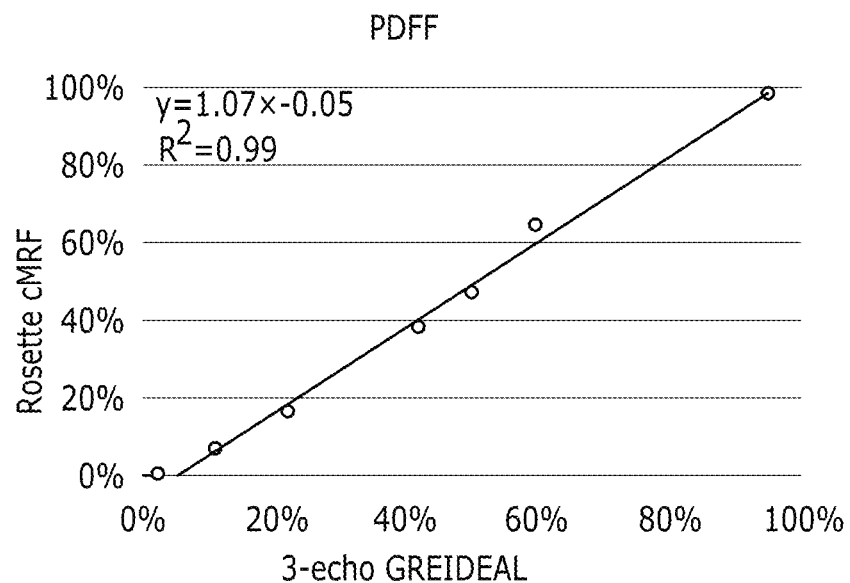
FIGS. 4A-4C are plots of PDFF measurements in the fat fraction phantom (FIG. 4A), and $T_1$ tissue property measurements (FIG. 4B), and $T_2$ tissue property measurements (FIG. 4C), in accordance with an example herein.
Figure 4B:
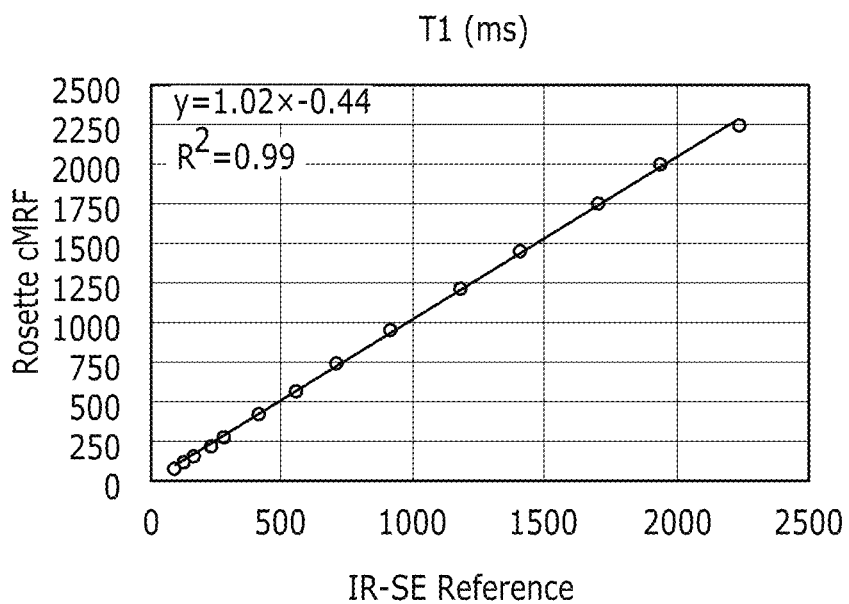
Figure 4C:
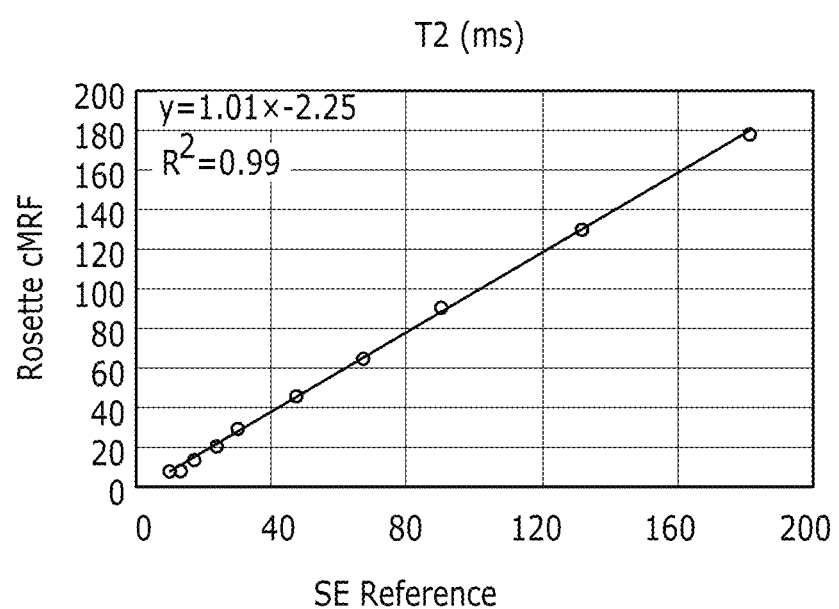

The results of the experiments are shown in FIGS. 4A-4C and FIG. 5. FIG. 4A is a plot of fat fraction, specifically PDFF, using the cMRF rosette trajectory 103 of FIG. 3. FIGS. 4B and 4C are plots of $T_1$ and $T_2$ measurements respectfully using rosette cMRF. In the heart, the averaged $T_1$ and $T_2$ values of all subjects measured using the current rosette cMRF signal technique, a sample spiral signal pattern cMRF technique, and conventional cardiac $T_1$ and $T_2$ mapping techniques are summarized in Table 1. Compared with MOLLI, the conventional $T_1$ mapping technique, spiral cMRF yielded similar $T_1$ values, while rosette cMRF generated significantly higher $T_1$ values, possibly due to reduced fat contamination. Both spiral and rosette cMRF yielded lower $T_2$ values compared with the conventional method, which is consistent with previous findings. The averaged PDFF in the septum was −0.8%. The resulting digital report of representative maps from one subject are shown in FIG. 5.

TABLE 1

Averaged $T_1$ and $T_2$ values in the entire mid-ventricular slice of 12 healthy subjects acquired using rosette cMRF compared with spiral cMRF and conventional methods (MOLLI for $T_1$ and $T_2$-prep bSSFP for $T_2$).

|  | $T_1$ (ms) | $T_2$ (ms) |
| --- | --- | --- |
| Rosette cMRF | 1081.8 ± 33 | 40.1 ± 1.3 |
| Spiral cMRF | 997.4 ± 53.6 | 36.9 ± 2.9 |
| Conventional | 991.5 ± 19.6 | 45.7 ± 2.6 |

Figure 5A:
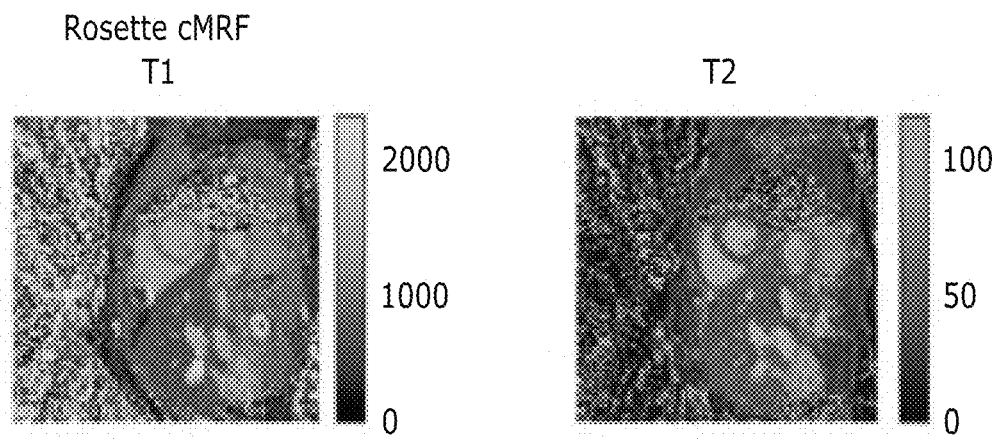
FIGS. 5A-5C are generated mappings of different tissue properties for three different cardiac tissue property mapping techniques.
Figure 5B:
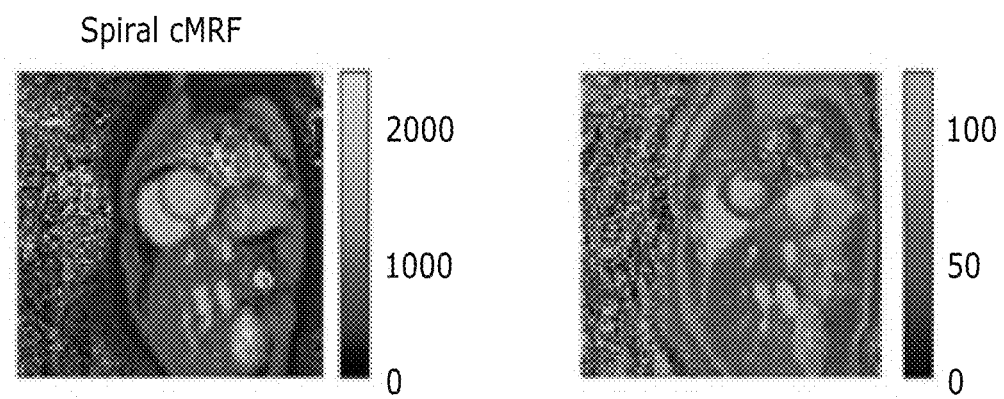
Figure 5C:
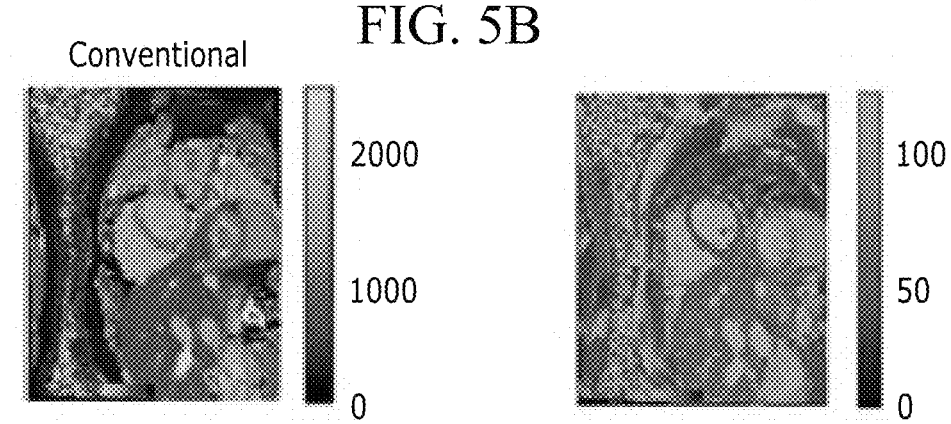

FIG. 5A illustrates the resulting $T_1$, $T_2$, M0 (water isolated), Fat M0 (fat isolated), and PDFF mappings using the rosette cMRF (i.e., segment level comparisons) of the present techniques. FIG. 5B illustrates the resulting $T_1$, $T_2$, and M0 (water isolated) mappings using a spiral pattern cMRF technique. As indicated, fat isolation and PDFF generation is not available with spiral pattern cMRF. FIG. 5C illustrates the results of conventional cardiac mapping techniques that resulted in only $T_1$ and $T_2$ mappings.

Figure 6:
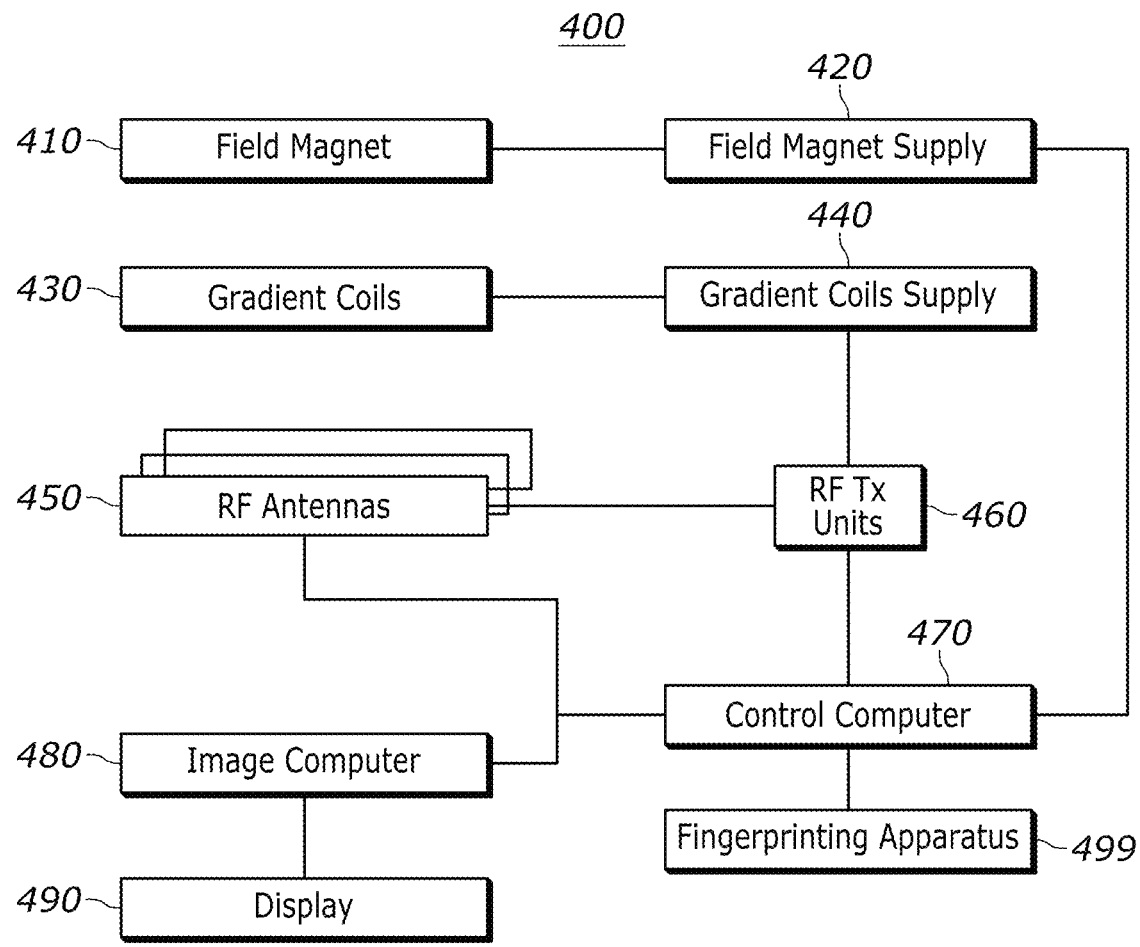
FIG. 6 illustrates an example MRF system which may include the MRF processing device of FIG. 1A and in which the techniques of FIG. 2 may be implemented, in accordance with an example.

FIG. 6 illustrates an example of a magnetic resonance scanning device in the form of a MRF system 400. The MRF system 400 may be implemented with the MRF processing device 100 of FIG. 1 as a fingerprinting apparatus 499 to facilitate the various processes and methods described herein, including segmented rosette trajectory analysis through MRF. Depending on the implementation, the fingerprinting apparatus 499 is and/or includes elements of MRF processing device 100 as described with regard to FIG. 1 above. In further implementations, the fingerprinting apparatus 499 performs example methods such as example method 200 as described above. While fingerprinting apparatus 499 is illustrated as part of MRF system 400 in one example, fingerprinting apparatus 499 may be a separate apparatus or apparatuses.

The system 400 includes one or more field magnets 410 and a field magnet supply 420. In some implementations, the field magnets 410 produce a uniform $B_0$ field—i.e. the main static magnetic field of the MRF system 400. However, in other implementations, the $B_0$ field is not uniform. In such implementations, the magnetic field instead varies over an object that the MRF system 400 analyzes. MRF system 400 further includes gradient coils 430 configured to emit gradient magnetic fields. The gradient coils 430 may be controlled, at least in part, by a gradient coil supply 440. In some implementations, the timing, strength, and orientation of the gradient magnetic fields may be controlled, and thus selectively adapted, during an MR procedure.

Further, the MRF system 400 includes a set of RF antennas 450 that generate RF pulses and receive resulting MR signals from an object that the MRF system 400 scans—i.e., the object to which the RF antennas 450 direct the RF pulses. In accordance with the processes and methods herein, the MRF system 400 controls how the RF pulses are generated and how the resulting MR signals are received, in particular by establishing RF pulses with pulse sequence parameters tailored to scan a region of interest (ROI) in a sample. In some implementations, the RF antennas 450 employs separate RF transmission and reception coils. Similarly, the RF antennas 450 may be controlled at least in part by a set of RF transmission units 460.

In some implementations, a control computer 470 controls some or all of the field magnet supply 420, the gradient coils supply 440, and/or the RF transmission units 460. That is, the control computer 470 may execute instructions received from the fingerprinting apparatus 499. In some examples, the control computer 470 is implemented within the fingerprinting apparatus 499. In further implementations, the control computer 470 is further programmed to control an MR device such as MRF processing device 100. In other implementations, control computer 470 is or includes elements of MRF processing device 100. Conventionally, the MRF system 400 employs the MR signals received from the RF antennas 450 to generate an MRF image, and thus may be subject to a transformation process. In some implementations, the transformation process is or is akin to a two dimensional fast Fourier transform (FFT) that generates pixilated image data. Depending on the implementation, an image computer 480 may perform the transformation. In other implementations, another, similar processing device performs the image transformation. Depending on the implementation, the display 490 may then display the image data. In some implementations, the display 490 may display some or all of the plots described with regard to FIGS. 4A-4C, and 5A-5C above. For example, the display 490 may display any of the images, plots, etc. generated by the process 200, by the MRF processing device 100, or otherwise described herein.

While FIG. 6 illustrates an example MRF system 400 that includes various components connected in various ways, one skilled in the art will appreciate that other MR systems may include other components connected in other ways.

In the foregoing specification, specific examples have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings. Additionally, the described embodiments/examples/implementations should not be interpreted as mutually exclusive, and should instead be understood as potentially combinable if such combinations are permissive in any way. In other words, any feature disclosed in any of the aforementioned embodiments/examples/implementations may be included in any of the other aforementioned embodiments/examples/implementations.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover, in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

It will be appreciated that some examples may be comprised of one or more generic or specialized processors (or "processing devices") such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the method and/or apparatus described herein. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used.

Moreover, an embodiment can be implemented as a computer-readable storage medium having computer readable code stored thereon for programming a computer (e.g., comprising a processor) to perform a method as described and claimed herein. Examples of such computer-readable storage mediums include, but are not limited to, a hard disk, a CD-ROM, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various examples for the purpose of streamlining the disclosure. This method of disclosure is not to be interpreted as reflecting an intention that the claimed examples require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

Moreover, the patent claims at the end of this patent application are not intended to be construed under 35 U.S.C. § 112(f) unless traditional means-plus-function language is expressly recited, such as "means for" or "step for" language being explicitly recited in the claim(s). The systems and methods described herein are directed to an improvement to computer functionality, and improve the functioning of conventional computers.

What is claimed:

1. A method for performing magnetic resonance fingerprinting (MRF), the method comprising:
   obtaining, using a magnetic resonance scanning device, MRF data of a region of interest in a sample and resulting from provision of a MRF pulse sequence to the sample, wherein obtaining the MRF data includes sampling a k-space using a rosette trajectory formed of a plurality of lobes;
   calculating a MRF dictionary of signal profiles based on the MRF pulse sequence applied;
   comparing the MRF dictionary to the MRF data to generate $T_1$ and $T_2$ maps from water corresponding to the region of interest;
   separating MRF data into a plurality of MRF data segments, each MRF data segment corresponding to a different segment of the plurality of lobes of the rosette trajectory, each different segment sampling a central region of the k-space;
   processing the plurality of MRF data segments to generate an isolated fat signal image, and generating, using the $T_1$ and $T_2$ maps from water and the isolated fat signal image, a proton density fat fraction map corresponding to the region of interest; and
   generating a report of the $T_1$ and $T_2$ maps and the proton density fat fraction map for display to a user.

2. A non-transitory computer-readable storage medium storing executable instructions that, when executed by a processor, cause a computer to:
   obtain, using a magnetic resonance scanning device, MRF data of a region of interest in a sample and resulting from provision of a MRF pulse sequence to the sample, wherein obtaining the MRF data includes sampling a k-space using a rosette trajectory formed of a plurality of lobes;
   calculate a MRF dictionary of signal profiles based on the MRF pulse sequence applied;
   compare the MRF dictionary to the MRF data to generate $T_1$ and $T_2$ maps from water corresponding to the region of interest;
   separate MRF data into a plurality of MRF data segments, each MRF data segment corresponding to a different segment of the plurality of lobes of the rosette trajectory, each different segment sampling a central region of the k-space;
   process the plurality of MRF data segments to generate an isolated fat signal image, and generate, using the $T_1$ and $T_2$ maps from water and the isolated fat signal image, a proton density fat fraction map corresponding to the region of interest; and
   generate a report of the $T_1$ and $T_2$ maps and the proton density fat fraction map for display to a user.

3. The method of claim 1, wherein the plurality of lobes of the rosette trajectory comprises at least 3 lobes.

4. The method of claim 3, wherein the plurality of lobes of the rosette trajectory comprises 8 lobes.

5. The method of claim 1, wherein comparing the plurality of MRF data segments to the MRF dictionary to generate an isolated fat tissue mapping comprises: projecting each MRF data segment onto a low dimensional subspace derived from the MRF dictionary.

6. The method of claim 1, wherein the MRF dictionary of signal profiles correspond to a cardiac rhythm.

7. The method of claim 1, wherein generating the report of the $T_1$ and $T_2$ maps and the proton density fat fraction map comprises: displaying the $T_1$ and $T_2$ maps and the proton density fat fraction map on a digital display.

8. The non-transitory computer-readable storage medium of claim 2, wherein the plurality of lobes of the rosette trajectory comprises at least 3 lobes.

9. The non-transitory computer-readable storage medium of claim 2, wherein the plurality of lobes of the rosette trajectory comprises 8 lobes.

10. The non-transitory computer-readable storage medium of claim 2, storing executable instructions that, when executed by the processor, cause the computer to project each MRF data segment onto a low dimensional subspace derived from the MRF dictionary.

11. The non-transitory computer-readable storage medium of claim 2, wherein the MRF dictionary of signal profiles correspond to a cardiac rhythm.

12. The non-transitory computer-readable storage medium of claim 2, storing executable instructions that, when executed by the processor, cause the computer to display the $T_1$ and $T_2$ maps and the proton density fat fraction map on a digital display.

* * * * *